United States Patent [19]

Grosskinsky et al.

[11] Patent Number: 4,634,584
[45] Date of Patent: Jan. 6, 1987

[54] STABILIZED SOLUTIONS OF HYDROXYLAMINE OR ITS SALTS IN WATER OR ALCOHOLS, AND THEIR PREPARATION

[75] Inventors: Otto-Alfred Grosskinsky; Elmar Frömmer; Josef Ritz, all of Ludwigshafen; Erwin Thomas, Freinsheim; Franz-Josef Weiss, Neuhofen, all of Fed. Rep. of Germany

[73] Assignee: BASF Aktiengesellschaft, Ludwigshafen, Fed. Rep. of Germany

[21] Appl. No.: 682,068

[22] Filed: Dec. 17, 1984

[30] Foreign Application Priority Data

Dec. 17, 1983 [DE] Fed. Rep. of Germany ....... 3345733

[51] Int. Cl.$^4$ .............................................. C01B 21/14
[52] U.S. Cl. .................................. 423/265; 423/387; 260/501.17; 252/188.28; 549/315
[58] Field of Search ................... 252/407, 403, 188.28; 260/501.17; 423/265, 387; 549/315

[56] References Cited

U.S. PATENT DOCUMENTS

| | | | |
|---|---|---|---|
| 3,145,082 | 8/1964 | Rausch et al. | 423/275 |
| 3,480,391 | 11/1969 | Carlos | 423/387 |
| 3,480,392 | 11/1969 | Carlos | 423/387 |
| 3,544,270 | 12/1970 | Carlos | 423/265 |

OTHER PUBLICATIONS

Lundberg, W. O. (Ed.), *Autoxidation and Antioxidants*, vol. II, Interscience Pblshrs., NY, (1962) pp. 506–508 and 510–513.

*Primary Examiner*—Herbert B. Guynn
*Assistant Examiner*—Matthew A. Thexton
*Attorney, Agent, or Firm*—Keil & Weinkauf

[57] ABSTRACT

Stabilized solutions of hydroxylamine or its salts in water or alcohols, containing the lactone of the formula

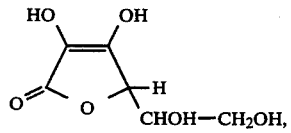

and their preparation.

4 Claims, No Drawings

STABILIZED SOLUTIONS OF HYDROXYLAMINE OR ITS SALTS IN WATER OR ALCOHOLS, AND THEIR PREPARATION

Solutions of hydroxylammonium salts decompose slowly at room temperature and more rapidly at elevated temperatures, this behavior being more pronounced in the case of solutions of free hydroxylamine. There has been no lack of attempts to stabilize solutions of hydroxylamine and its salts in order to achieve a longer shelf life. For example, according to U.S. Pat. No. 3,544,270, urea derivatives are used as stabilizers. U.S. Pat. No. 3,480,391 discloses that amidoximes are suitable stabilizers, while U.S. Pat. No. 3,480,392 recommends hydroxamic acids for this purpose. Furthermore, U.S. Pat. No. 3,145,082 discloses the use of chelate-forming agents, such as sodium ethylenediaminetetraacetate, as stabilizers. The stabilizers used to date are unsatisfactory.

It is an object of the present invention to provide stabilized solutions of hydroxylamine or its salts which are stable over a prolonged period and in which, in particular, the decomposition of free hydroxylamine is minimized, the solution not becoming discolored during storage.

We have found that this object is achieved by stabilized solution of hydroxylamine or its salts in water or alcohols, which contain the lactone of the formula

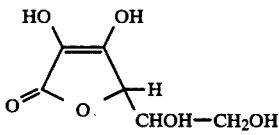

The present invention furthermore relates to a process for the preparation of stabilized solutions of hydroxylamine or its salts by the addition of stabilizers, wherein the molecular oxygen dissolved in the solution to be stabilized is removed from this solution by treatment with nitrogen which is free of molecular oxygen, and the lactone of the formula I is then added.

The solutions of hydroxylamine or its salts which have been stabilized according to the invention have the advantages that they are stable over a longer period than prior art solutions, and in particular the decomposition of free hydroxylamine is reduced to a minimum, and that they do not become decolorized during storage.

According to the invention, a solution of hydroxylamine or one of its salts in water or an alcohol, eg. a $C_1$–$C_4$-alkanol, is used as the starting material. Examples of suitable salts of hydroxylamine are those with a strong mineral acid, such as sulfuric acid, nitric acid or hydrochloric acid, or those with fatty acids, eg. acetic acid or propionic acid. Because of the difference in solubilities, hydroxylamine is preferably present in the form of a solution in water or an alcohol whereas its salts are preferably present as aqueous solutions. The content of hydroxylamine or its salts is, as a rule, from 10 to 70% by weight. Particularly preferably, aqueous hydroxylamine solutions are used, such starting solutions generally having a pH of from 8 to 11.

According to the invention, the stabilizer used is the lactone of the formula

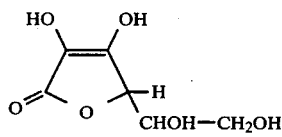

The lactone of the formula I is disclosed in Beilstein E III/VI 1B, 3038-3047, and, advantageously, is used in amounts of from 0.005 to 1, in particular from 0.01 to 0.1, % by weight, based on the solution to be stabilized.

Stabilized solutions of hydroxylamine or its salts in water or in alcohols are prepared, according to the invention, by a method in which the molecular oxygen dissolved in the solution to be stabilized is first displaced from this solution by treatment with nitrogen which is free of molecular oxygen. This is achieved by, for example, passing oxygen-free nitrogen through the solution to be stabilized, for example for from 5 to 10 minutes. The nitrogen used advantageously contains less than 2 ppm of molecular oxygen. The lactone of the formula I is then added, and is dissolved in the said solution, the temperature advantageously being kept at from 5° to 40° C. during this procedure. It is also possible to add the stabilizer in the form of a solution, for example in water or in a $C_1$–$C_4$-alkanol, to the solution to be stabilized.

It is of course advantageous if the solution to be stabilized is prevented from becoming contaminated with heavy metals, in particular copper or noble metals. Advantageously, the content of such heavy metals should be less than 1 ppm. It is also advantageous to exclude highenergy radiation by means of suitably colored glass containers, and to store the stabilized solutions at <40° C., for example at from 5° to 20° C.

Stabilized solutions of hydroxylamine or its salts are useful for the preparation of oximes.

The Example which follows illustrates the subject of the invention.

EXAMPLE

Oxygen-free nitrogen is passed through an aqueous solution of hydroxylamine at 20° C. for 10 minutes, after which the stabilizer is added. The concentration of hydroxylamine, the type and amount of the stabilizer added and the results achieved as a function of time are shown in the Table below.

TABLE

| Stabilizer | °C. | | | | |
|---|---|---|---|---|---|
| 2,3-Dihydrohexono-1,4-lactone | 25 | 0 | 293 | 462 | hours |
| 25 mg/mole of $NH_2OH$ of $NH_2OH$ | | 540.15 | 539.98 | 535.63 | g/l |

We claim:

1. An oxygen-free stabilized solution of hydroxylamine or its salts in water or an alcohol which is stable over a prolonged period and in which the solution does not become discolored, which contains the lactone of the formula

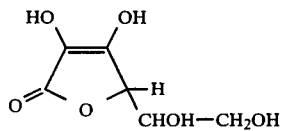

2. A stabilized solution as claimed in claim 1, which contains from 0.005 to 1% by weight, based on the solution to be stabilized, of a lactone of the formula I.

3. A stabilized solution as claimed in claim 1, wherein an aqueous solution containing from 10 to 70% by weight of hydroxylamine is used as a starting material.

4. A stabilized solution as claimed in claim 1, which contains from 0.01 to 0.1% by weight of the lactone of the formula I.

* * * * *